(12) United States Patent
Verkruijsse et al.

(10) Patent No.: US 10,987,008 B2
(45) Date of Patent: Apr. 27, 2021

(54) DEVICE, METHOD AND COMPUTER PROGRAM PRODUCT FOR CONTINUOUS MONITORING OF VITAL SIGNS

(71) Applicant: KONINKLIJKE PHILIPS N.V., Eindhoven (NL)

(72) Inventors: Willem Verkruijsse, Veldhoven (NL); Mukul Julius Rocque, Eindhoven (NL); Mohammed Meftah, Tilburg (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 392 days.

(21) Appl. No.: 16/060,567

(22) PCT Filed: Dec. 15, 2016

(86) PCT No.: PCT/EP2016/081094
§ 371 (c)(1),
(2) Date: Jun. 8, 2018

(87) PCT Pub. No.: WO2017/108547
PCT Pub. Date: Jun. 29, 2017

(65) Prior Publication Data
US 2019/0000330 A1 Jan. 3, 2019

(30) Foreign Application Priority Data
Dec. 21, 2015 (EP) ..................................... 15201655

(51) Int. Cl.
*A61B 5/024* (2006.01)
*A61B 5/00* (2006.01)
(Continued)

(52) U.S. Cl.
CPC ........ *A61B 5/02416* (2013.01); *A61B 5/0033* (2013.01); *A61B 5/0077* (2013.01);
(Continued)

(58) Field of Classification Search
CPC . A61B 5/02416; A61B 5/02438; A61B 5/681; A61B 5/6824; A61B 5/6831
See application file for complete search history.

(56) References Cited

U.S. PATENT DOCUMENTS

| | | | |
|---|---|---|---|
| 8,932,217 | B2 | 1/2015 | Gibson |
| 10,276,036 | B2 | 4/2019 | Lee |

(Continued)

FOREIGN PATENT DOCUMENTS

| | | |
|---|---|---|
| KR | 2014031589 | 3/2014 |
| WO | 2009136341 | 11/2009 |

(Continued)

OTHER PUBLICATIONS

Wang, et al., "Unsupervised Subject Detection via Remote PPG", IEEE Transactions on Biomedical Engineering, vol. 62, No. 11, Nov. 2015.
(Continued)

*Primary Examiner* — Puya Agahi (57) ABSTRACT

A wearable device for continuous health monitoring, the device comprising: a band for conforming to a first body part of a subject; an imaging unit, the imaging unit being connected in the band, wherein the imaging unit is configured to acquire a sequence of images from the subject's body, wherein the device is operable in a contact mode and in a non-contact mode, i. wherein in the contact mode the imaging unit is in substantial close 5 proximity to the first body part of the subject so as to acquire the sequence of images of an area of the first body part; wherein in the non-contact mode the imaging unit is in a remote position to acquire the sequence of images of a second body part of the subject; a controller unit configured to derive a PPG signal from the acquired sequence of images according to a first process when the device is in the contact mode and according to a second process when 10 the device is in the (Continued)

non-contact mode, the PPG signal being indicative of the health of the subject; wherein the controller unit, during operation of the wearable device, is configured to check at least one pre-determined condition in order to determine if the PPG signal is to be derived according to the first process or the second process.

15 Claims, 8 Drawing Sheets

(51) Int. Cl.
    *A61B 5/1171*     (2016.01)
    *G06K 9/00*     (2006.01)

(52) U.S. Cl.
    CPC ........ *A61B 5/02438* (2013.01); *A61B 5/1176* (2013.01); *A61B 5/681* (2013.01); *A61B 5/6824* (2013.01); *A61B 5/6831* (2013.01); *A61B 5/7221* (2013.01); *G06K 9/00268* (2013.01); *A61B 2562/0219* (2013.01)

(56) References Cited

U.S. PATENT DOCUMENTS

| | | |
|---|---|---|
| 2013/0303921 A1 | 11/2013 | Chu |
| 2014/0243622 A1 | 8/2014 | Crowe |
| 2015/0282724 A1 | 10/2015 | McDuff |

FOREIGN PATENT DOCUMENTS

| | | |
|---|---|---|
| WO | 2011043631 | 4/2011 |
| WO | 2013030745 | 3/2013 |
| WO | 2014015378 | 1/2014 |
| WO | 2015/086338 | 6/2015 |
| WO | 2015121070 | 8/2015 |

OTHER PUBLICATIONS

Liu, et al., "A novel method based on two cameras for accurate estimation of arterial oxygen saturation", BioMed Eng Online 2015, 14:52.

DEVICE, METHOD AND COMPUTER PROGRAM PRODUCT FOR CONTINUOUS MONITORING OF VITAL SIGNS

CROSS REFERENCE TO RELATED APPLICATIONS

This application is the U.S. National Phase application under 35 U.S.C. § 371 of International Application No. PCT/EP2016/081094, filed Dec. 15, 2016, published as WO 2017/108547 on Jun. 29, 2017, which claims the benefit of European Patent Application Number 15201655.6 filed Dec. 21, 2015. These applications are hereby incorporated by reference herein.

FIELD OF THE INVENTION

The present invention relates to monitoring of vital signs of a subject and in particular to a device, method and computer program product for continuous monitoring of the vital signs.

BACKGROUND OF THE INVENTION

Continuous monitoring of vital signs, such as heartrate (HR), is increasingly ubiquitous for non hospitalized individuals. Such long-time information can be used in predictive care. HR can be detected in an ambulatory mode (a person walking or running) as well as in a static mode (a person seated behind a desk).

Currently, continuous monitoring is typically done with contact probes (PPG, capacitive ECG, etc.) or in wearable form factors (wristband, chest belt, skin patch, ear probe, etc.). Alternatively, for non-ambulatory subjects, continuous monitoring may be performed by a camera (e.g. premature infants in incubators, or bed-ridden patients in general wards) having very specific benefits.

However, each of these has its own disadvantages. For instance, battery problems and skin irritation are major reasons with wearable form factors which do not facilitate continuous monitoring. One can imagine that the wearable device will need to be charged after couple of hours/days, and hence there is interruption in the monitoring. Also, the user needs to give the skin some rest as it is not very convenient to wear a device continuously for days. Though, the disadvantage of the wearable device is of course solved in the non-contact monitoring in terms of skin irritation and power management but the disadvantage of this monitoring technique is that it becomes very cumbersome when the subject is ambulatory because the unit for non-contact monitoring cannot be brought along with the patient easily. Thus, both the systems have their own advantages and disadvantages.

SUMMARY OF THE INVENTION

Therefore, it is an object of the present invention to provide a wearable device, a method and computer program product that substantially alleviates or overcomes the aforementioned problems.

In a first aspect of the invention, a wearable device for continuous health monitoring, the device comprising: a band for conforming to a first body part of a subject; an imaging unit, the imaging unit being connected in the band, wherein the imaging unit is configured to acquire a sequence of images from the subject's body, wherein the device is operable in a contact mode and in a non-contact mode, wherein in the contact mode the imaging unit is in substantial close proximity to the first body part of the subject so as to acquire the sequence of images of an area of the first body part; wherein in the non-contact mode the imaging unit is in a remote position to acquire the sequence of images of a second body part of the subject; a controller unit configured to derive a PPG signal from the acquired sequence of images according to a first process when the device is in the contact mode and according to a second process when the device is in the non-contact mode, the PPG signal being indicative of the health of the subject; wherein the controller unit, during operation of the wearable device, is configured to check at least one pre-determined condition in order to determine if the PPG signal is to be derived according to the first process or the second process.

Various examples of the band include but are not limited to a flexible band, a strap, a cuff, a necklace, a head band, around ear hook arrangement. These wearing means/options can be used to conform to a body part of the subject. For instance, the wrist worn device will be conformed around the wrist of the user. Similarly, a necklace will conform around the neck of the subject.

In an embodiment, the first body part and the second body part are different, such as first body part is a wrist and the second body part is a face. In an alternate embodiment of the invention, the first body part and the second body part can be same, for instance chest of the user. In this case in the contact mode, the device will only capture sequence of images of an area (limited) of the chest. While in the non-contact mode, the device can view the chest and capture the sequence of images accordingly for further derivation of PPG signal. In both the cases, i.e. contact/non-contact mode, the imaging unit captures sequence of images of an area of the body part. In the contact mode, the imaging unit captures the (limited) area of the body part that is directly below the imaging unit when in contact with the skin. In other words, the imaging unit will capture the sequence of images of area of the first body part that is directly in front of the imaging unit when the imaging unit is placed on the first body part. For instance, skin of the wrist when worn as wrist worn device. In the non-contact mode, the area can be the body part itself, such as face, chest, etc. Since, in the non-contact mode, the device is at a distance, it is possible to capture the whole body part that is viewed by the imaging unit.

The wearable device as described above has numerous advantages. The wearable device now captures relevant PPG information continuously in a user-convenient way. For instance, for continuous measurement of heartrate (HR), the user can now choose between wearing it on the body part, such as wrist, and placing the device on a desk. In both the use cases, the HR information will be captured and an overall measurement can thus be provided to the user for his assessment. Further, the switch between the contact mode and non-contact mode is performed automatically and hence the device overall is very easy to handle and use. In addition to monitoring vital signs continuously, the user also gets a break from wearing the device and hence avoids the skin irritation issues. Also, since the device can be used in the non-contact mode, the user can simultaneously charge the device in order to solve power management issues. Thus, without expensive batteries, the problem of power management is solved by choosing the right mode of monitoring.

In a further embodiment, the second body part is a face of the subject and the controller unit is configured to detect presence of at least one facial feature of the subject in the acquired image in order derive the PPG signal according to the second process and wherein when the presence of the facial feature is not detected, the controller unit is configured to derive the PPG signal according to the first process, wherein detecting the presence or the non-presence of the at least one facial feature of the subject is the at least one pre-determined condition. In a preferred embodiment, focusing is desired when the imaging unit faces the user. This can be implemented with manual focusing or auto-focusing. In an embodiment of the invention, the focusing range is limited to 0.5 to 1 meter in order to exclude accidentally capturing of PPG information of a person farther away than the subject.

In a further embodiment, if the controller unit detects that the user is moving out the viewing range of the non-contact mode detection, then a signal such as flashing of LED in a particular color or audio feedback may be provided to switch to the contact mode, i.e. wearable mode. Alternatively, the user can be guided to come back to the viewing range.

In a further embodiment, the device further includes an ambient light sensor for sensing an ambient light, wherein the controller unit is configured to derive the PPG signal according to the second process when the ambient light is above a pre-determined ambient light threshold and wherein when the ambient light is below the pre-determined ambient light threshold, the controller unit is configured to derive the PPG signal according to the first process, wherein checking the ambient light is above or below the pre-determined ambient light threshold is the at least one pre-determined condition.

In a further embodiment, the imaging unit is removably connected to the band. This gives additional advantage as the module can be just placed at the desk in a docking station, wherein the imaging module can be simultaneously charged. In an embodiment of the invention, the imaging unit and the controller unit can be housed in a single housing and the housing can be placed in the band. Such housing will further include a battery/batteries that can be charged while the housing is placed on a docking station. In a further embodiment of the invention, the removable imaging unit is configured to acquire the sequence of images from being attached to another entity, the another entity being different than the band. The imaging unit/the housing can have connector, such as a USB connector which can be connected to another device, such a desktop, laptop in order to get charged. In an alternate embodiment, a light source (Near Infra-Red) is arranged in the another entity or the wearable device in order to facilitate remote monitoring (non-contact mode) in the dark, such as sleep state, or measurements that require dedicated wavelengths (Near Infra-Red for $SpO_2$ measurements).

In a further embodiment, the band comprises an aperture, the removable imaging unit being placed, in the contact mode, above the aperture such that the imaging unit is able to acquire the sequence of images form the area of the subject which is in front of the aperture. In other words, the sequence of the images are captured of the area of the first body part.

In a further embodiment, the device is further arranged to derive vital sign information from the PPG signal derived from acquired sequence of images in each mode. Various examples of vital sign information include but are not limited to HR information, heart rate variability, respiration rate, arterial oxygen saturation (SpO2). It may be apparent to a person skilled in the art that such vital sign information points can be further used to derive stress information, sleep pattern, etc.

In a further embodiment, the imaging unit in communication with the controller unit is configured to recognize the subject in the non-contact mode by detecting one or more facial features of the subject. For instance, a user profile can be stored in a memory unit of the device such that when the device detects the facial features of the user, it further recognizes if the user is indeed the same user whose PPG signal needs to be acquired. One can imagine this brings additional intelligence in the device. To further elaborate with help of an example, there may be two users, user A and user B, in a room. User A is wearing the wearable device whose PPG signal is being monitored and now he would like to use the device in the non-contact mode. Thus, the imaging unit now detects facial features of possibly two people in the room. Thus, recognizing user A is advantageous to further acquire PPG signal in order to monitor his vitals continuously. It may be apparent to a person skilled in the art that without this intelligence, the system may continue to acquire the PPG information of the other user B and hence does not give the right overall analysis to the user A in the end. It should be apparent to a person skilled in the art that multiple such user profiles can be stored in the device.

In a further embodiment, if the user A is not recognized, then the controller unit switches to a standby mode in order to save battery power of the wearable device.

In a further embodiment, the wearable device includes an illumination unit, such as a LED, for illuminating the subject's skin in the contact mode.

In a further embodiment, the controller unit is configured to check if a PPG signal is derivable from the sequence of images in the contact mode, wherein the control unit is configured to switch off the illumination unit in absence of the PPG signal. This facilitates better power management of the wearable device.

In a further embodiment, the wearable device includes an accelerometer to provide motion information of the subject, wherein the controller unit is arranged to instruct the imaging unit to acquire the sequence of images in the contact mode upon receiving motion information. This facilitates better power management of the wearable device.

In a preferred embodiment, the wearable device is a wrist worn device and hence is arranged to get PPG information from the wrist (the first body part) of the user. However, other form factors of the wearable device are also possible, such as arm worn device, a headphone, an earphone, a chest worn device, a head-worn device, and a foot worn device, ankle worn device, neck worn device, etc. Alternatively, a mobile device, such as a smart phone including a camera, along with a strap/band can be used as wearable device.

In a further embodiment, in the non-contact mode, the controller unit is further configured to provide feedback to the subject such that the subject can place the imaging unit in a preferred position, wherein the preferred position being a position in which the imaging unit captures facial features of the subject in order to acquire the sequence of images. The feedback may be visual, such as flashing of LEDs, audio, such as beeps or combination. Advantageously, such a feature ensures that the imaging unit is a right position to gather sufficient PPG information from the images.

In a second aspect of the invention, a method for continuous monitoring is provided. The method includes acquiring a sequence of images from the subject's body, wherein the images are being acquired by an imaging unit; wherein the imaging unit is either placed in a contact mode or in a non-contact mode, wherein in the contact mode the imaging unit is in substantial close proximity to a first body part of the subject so as to acquire the sequence of images of an area of the first body part and wherein a first process is used by a controller unit to derive a PPG signal when in the contact mode; and wherein in the non-contact mode the imaging unit is in a remote position to acquire the sequence of images of a second body part of the subject and wherein a second process is used by the controller unit to derive a PPG signal when in the non-contact mode; checking at least one pre-determined condition, the check being performed by the controller unit; and deriving the PPG signal according to the first process or the second process based on the outcome of the check, wherein the PPG signal is derived by the controller unit.

In a third aspect of the invention, there is provided a computer program product which comprises computer readable program code embodied therein, when executed by the wearable device/controller unit as discussed above to perform the steps of the method disclosed herein.

Preferred embodiments of the invention are defined in the dependent claims. It should be understood that the claimed method and the claimed computer program product can have similar preferred embodiments and the corresponding advantages as the claimed device and as defined in the dependent method claims.

To summarize various aspects of the invention are aimed at providing a device that can be both used in the contact mode and in the non-contact mode in order to facilitate continuous monitoring by acquiring PPG signal in both the modes. The controller unit of the device is configured to derive the PPG signal according to either the first or the second process depending on whether at least one pre-determined condition is fulfilled. In other words, the controller unit checks for a pre-determined condition and based on the outcome of the check derives the PPG signal either by the first process or by the second process.

BRIEF DESCRIPTION OF THE DRAWINGS

These and other aspects of the invention will be apparent from and elucidated with reference to the embodiments described hereinafter. In the following drawings

DETAILED DESCRIPTION OF THE INVENTION

Figure 1:
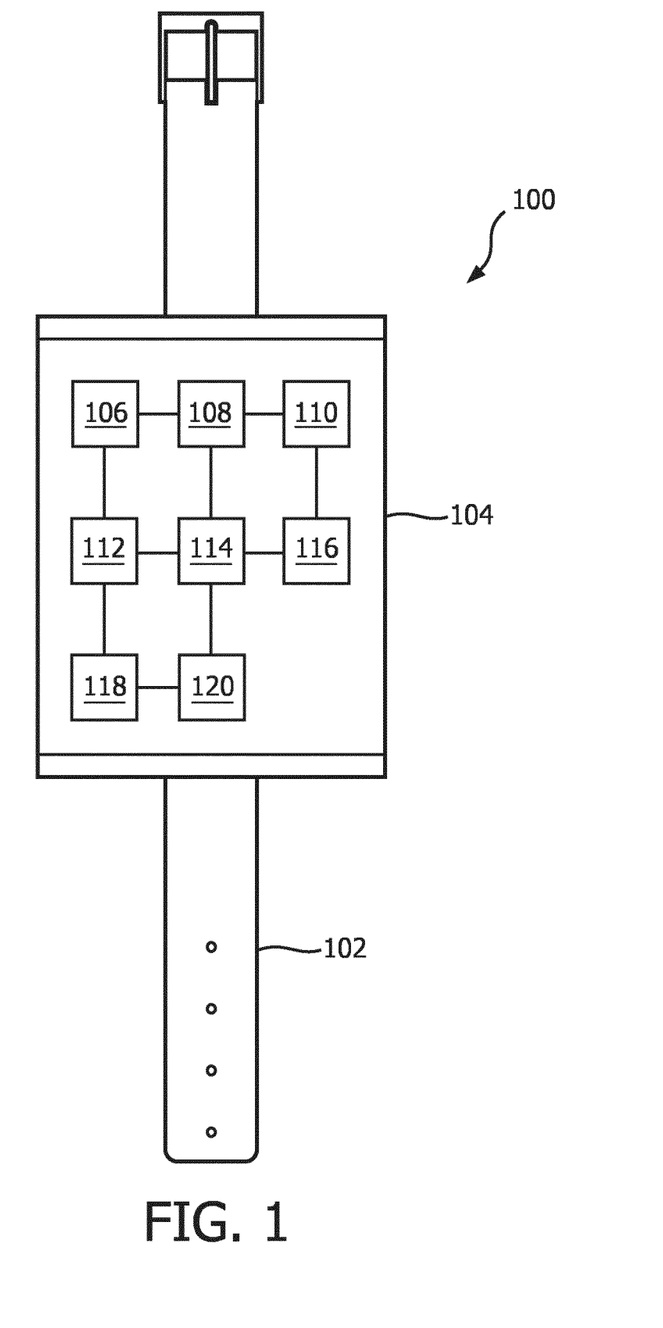
FIG. 1 shows a device for continuous monitoring of a subject according to an embodiment of the invention.

FIG. 1 shows a device for continuous monitoring of a subject according to an embodiment of the invention. The device 100 includes a band 102 and a device body 104 (also may be referred to as housing 104). The device body 104 further includes an imaging unit 106, a controller unit 108, an ambient light sensor 110, an illumination unit 112, an accelerometer 114, a memory unit 116, one or more batteries 118 and a display unit 120.

Prior to explaining the invention, certain terminologies used throughout the draft are explained below for the sake of clarity.

Figure 3A:
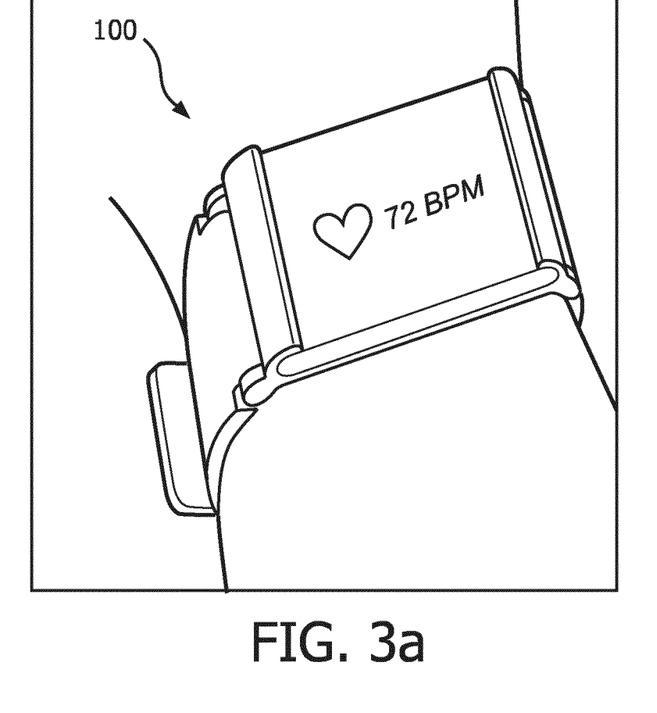
FIGS. 3a and 3b show the device in a contact mode according to an embodiment of the invention.
Figure 3B:
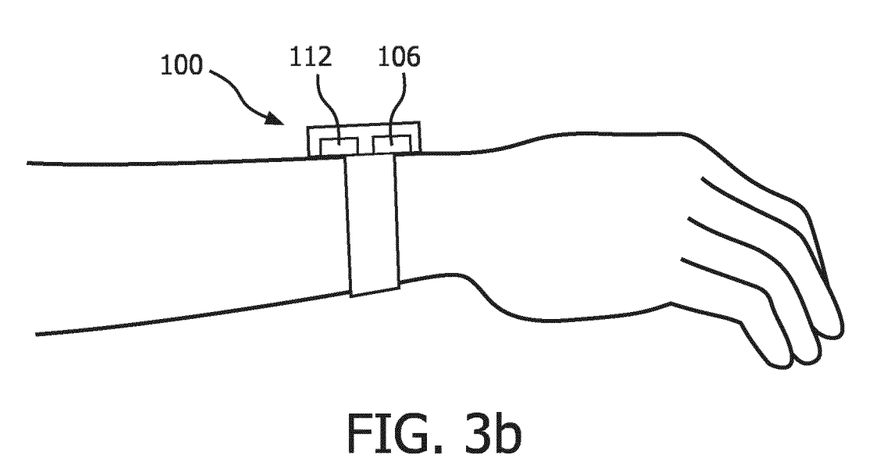

Contact Mode: In this mode the device 100 is configured to be in contact with skin of the body/body part. In this mode the imaging unit 106 of the device 100 will be placed such that it touches the skin of the user/subject. In the current embodiment of the invention, the device 100 is a wrist worn device 100 and hence the imaging unit 106 will touch the wrist (first body part) of the user. The contact mode is also depicted in FIG. 3a and FIG. 3b. In the contact mode a first process/algorithm is used to derive the PPG signal. One of such process to derive the PPG signal in the contact mode is explained in detail in conjunction with FIG. 5.

Figure 4A:
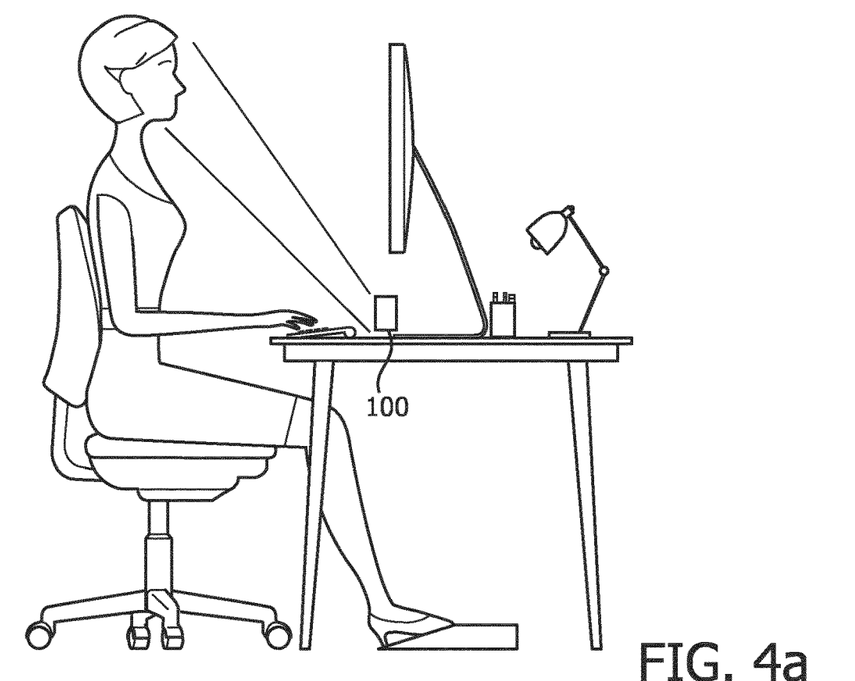
FIGS. 4a and 4b show the device in a non-contact mode according to an embodiment of the invention.
Figure 4B:
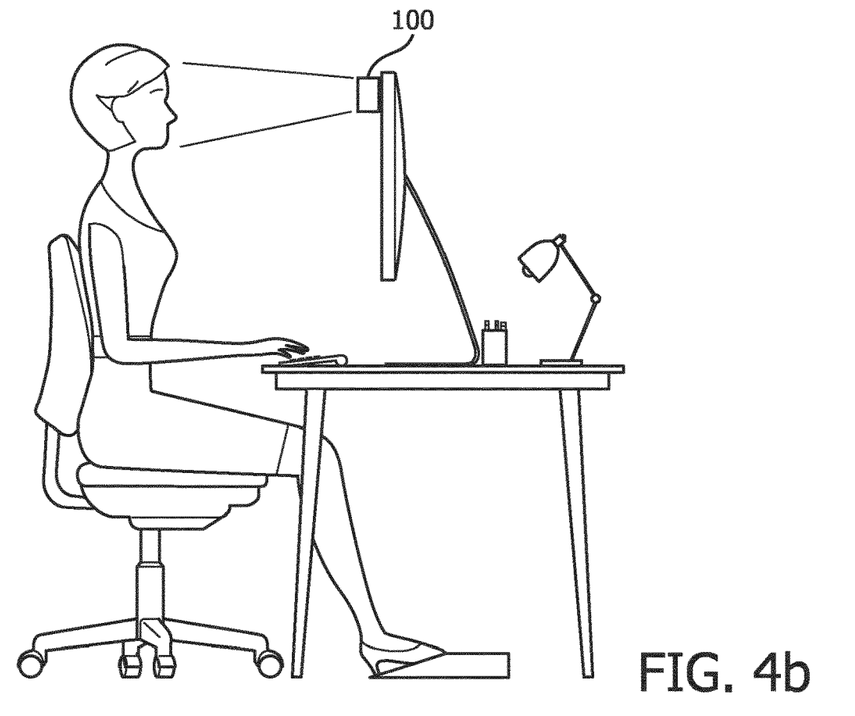

Non-contact Mode: In this mode the device 100 is configured to be at a distance/remote from the user. To further elaborate, in this mode, the device 100 does not touch the skin of the user. The device 100 can be placed at his desk (FIG. 4a), on a desktop screen (FIG. 4b), etc. such that the device 100 can capture images of the subject's body, preferably face (second body part), that are useful for deriving PPG signal. In the non-contact mode a second process/algorithm is used to derive the PPG signal. One of such process to derive the PPG signal in the remote is explained in WO2013030745A1.

Working of the device 100 will now be explained in conjunction with a method 200 (FIG. 2) executed by the controller unit 108.

Figure 2:
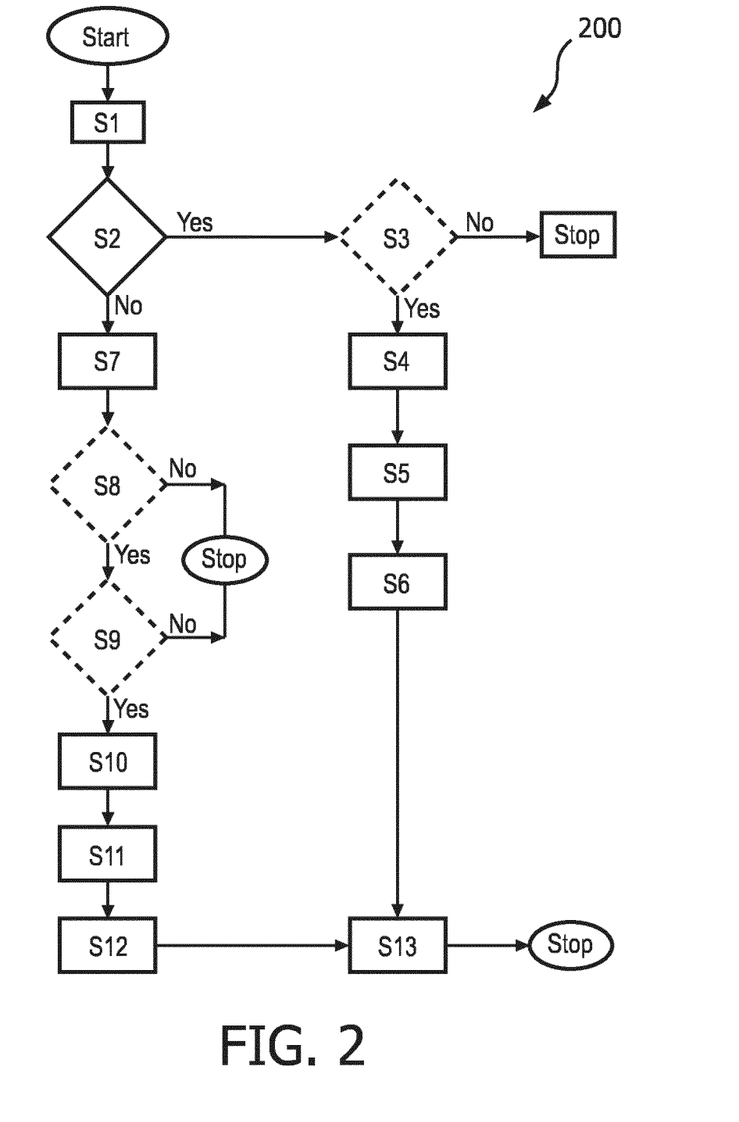
FIG. 2 shows a flowchart depicting a method executed by a controller unit of the device of FIG. 1, according to the embodiment of the invention.

During the operation of the device 100, the imaging unit 106 starts to capture/acquire a sequence of images at S1. The imaging unit 106 can be a standard digital camera, such as CMOS, CCD. In other words, the imaging unit 106 can be any digital sensory array and a corresponding imaging optics.

At S2, the controller unit 108 checks if at least one facial feature is detected (i.e. presence or non-presence of the facial feature). In the current embodiment of the invention, detecting at least one facial feature is the pre-determined condition. In an embodiment of the invention device 100 can have pre-stored list of facial features, such as nose, eyes, cheeks, etc. that the controller unit 108 searches in the acquired images. In an embodiment of the invention, the controller unit 108 uses a pre-defined method to detect facial features of the subject. The method is further described in the paper "Unsupervised Subject Detection via Remote PPG, authored by Wenjin Wang; Stuijk, S.; de Haan, G; at Electron. Syst. Group, Eindhoven Univ. of Technol., Eindhoven, Netherlands and published in Biomedical Engineering, IEEE, Volume: 62 Issue: 11". The document can further be located at (http://ieeexplore.ieee.org/xpl/articleDetails.jsp?arnumber=7114247). Further, the controller unit 108 can also guide the user such that the user places the housing 104 in such a way that the imaging unit 106 captures the facial features. Various ways, such as beeping tone, flashing an LED, etc. can be envisaged to guide the person to place the housing 104 appropriately. Once, the user has placed the housing 104 at the right position, the controller unit 108 indicates the user with an audio signal, or change in color of the LED.

If at least one facial feature is detected in the acquired sequence of images, the controller unit 108 at S3 optionally can further recognize the subject. Various known facial recognition algorithms/image recognition algorithms are known to the person skilled in the art. At least one of such known facial recognition algorithm can be used. In an embodiment, the memory unit 116 can store (in form of a data structure, database) various facial features of the subject, which can be used in the real time recognition of the subject. It is known in the art of facial/image recognition algorithms that captured facial features are compared with the facial features stored in the database to recognize the subject.

If at S3, the user is recognized or if the facial feature is detected, the controller unit 108 switches to a non-contact mode, at S4, and instructs the imaging unit 106 to continue to acquire the set of images. In the non-contact mode, the controller unit 108 uses the second process, at S5, as explained in WO2013030745A1 to derive the PPG signal from the acquired images. At S6, various vital sign information values can be derived from the derived PPG signal. One of the vital sign information derived in the current embodiment is heart rate (HR). Various methodologies to derive HR information from the PPG signal are already known to the skilled person. In the current embodiment of the invention, the controller unit 108 can further store the HR information in the memory unit 116.

Though in the current embodiment of the method 200, the detection of the non-contact mode is confirmed by detecting at least one facial feature, it is also possible that such a confirmation can be made by detecting ambient light (pre-determined condition). The ambient light sensor 110 is configured to detect the ambient light around the imaging unit 106. The controller unit 108 in communication with the ambient light sensor 110 can check if the ambient light is above a pre-determined ambient light threshold and if the detected ambient light is indeed above than the pre-determined ambient light threshold, then the controller unit 108 can proceed to S4 and same steps as discussed above, i.e. S4-S6 will be performed. Thus, in both the possibilities discussed above, the pre-determined condition is checked, i.e. either checking the presence (or non-presence) of facial features in the acquired image or checking the ambient light is above (or below) the pre-determined ambient light threshold and consequently based on the outcome of the check a mode of operation (contact/non-contact) is determined and which in turn determines the process (either the first process or the second process) to be selected to perform the derivation of the PPG signal. In an alternate embodiment a combination of facial detection and ambient light sensing can also be performed to confirm/detect the non-contact mode.

In an embodiment of the invention, in the non-contact mode, the imaging unit 106 will use ambient illumination and will not use any dedicated in-built illumination and thus will be power efficient. In an alternate embodiment of the invention, an additional illumination may be used based on the situation, for instance, the additional illumination may be required while monitoring the subject in the night.

However, at S2, if the controller unit 108 does not detect any facial feature of the subject, then at S7, the controller unit 108 switches to the contact mode. Thus, at S7, the imaging unit 106 continues to acquire the images, which will be processed by the controller unit 108 using the first process to derive the PPG signal.

In this mode, the controller unit 108 further instructs the illumination unit 112 to light up the area on the wrist of the user in order to acquire images from which the PPG signal can be derived thereafter. In this mode, the controller unit 108 further checks at least one condition (S8; S9) before continuing to acquire images in order to save the battery. Thus, when switched to the contact mode, at S8, the controller unit 108 further checks if there is motion information indication from the accelerometer 114. For instance, a motion threshold can be set and if the motion information is above the motion threshold, then it is indicative that imaging unit 106 is in contact with the subject's body part. Such an indication provides useful information that indeed the imaging unit 106 is in contact with the subject's body part and not with any other non-living object, such as a desk. It may be useful that after it is detected that the imaging unit 106 is not in the non-contact mode, i.e. now in contact mode, to further check if it is indeed in contact with the subject. If not, the illumination unit 112 and the imaging unit 106 can be switched OFF, thereby saving power.

The accelerometer 114 generally provides three-dimensional accelerometer data, i.e. a separate accelerometer signal for each of three orthogonal directions indication the acceleration in the respective direction. However, the invention also works with other accelerometer data, e.g. a single accelerometer signal (i.e. one-dimensional accelerometer data) or two-dimensional accelerometer data, as long as the desired motion information in some way reflected in the accelerometer data.

At S8, if it is detected that the imaging unit 106 is on the subject's wrist, a further check (S9) can be performed. The controller unit 108 further checks if the PPG signal can be derived from the images captured by the imaging unit 106. If at S9, it is detected that the PPG information cannot be derived using the first process, then the controller unit 108 switches OFF the illumination unit 112 and the imaging unit 106. The advantage of the switching OFF the illumination unit 112 remains the same, i.e. saving battery power. Though, in the current embodiment, both the conditions (S8; S9) are checked by the controller unit 108, it may be apparent that any one of the checks can be executed by the controller unit 108. In an alternate embodiment of the invention, both S8 and S9 can be optional steps.

Once at S9, it is confirmed that the imaging unit 106 is in contact with the user's skin, the controller unit 108 instructs the imaging unit 106, at S10, to continue to acquire the sequence of images. In the contact mode, at S11, the controller unit 108 executes the first process described in detail in conjunction with FIG. 5 to derive the PPG signal. Thereafter, at S12, the vital sign information, i.e. HR, is derived from the PPG signal. The derived vital sign information is stored in the memory unit 116. As explained earlier, there are various methodologies known to the skilled person to derive HR information from the PPG signal. Thereafter, at S13, HR information collected at S6 and S12 is collated to facilitate continuous monitoring of the heart rate. This is also depicted in FIG. 6. The transition depicted in FIG. 6 is the time lost when the device 100 is switches from one mode to another. It may be appreciated by a person skilled in the art that such a small duration (such as, 5 seconds or even 1 minute) will not deter the overall continuous HR monitoring of the subject. The overall HR information in form of a graphical display can be provided to the subject via the display unit 120. Various display technologies include but are not limited to LCD technology, LED technology, electronic ink (E Ink), etc. can be used in the display unit 120.

The device 100 as described above can be worn such that the imaging unit 106 contacts the wrist of the user in the contact mode. Further, the device 100 along with the band 102 can be placed at the desk such that the imaging unit 106 captures the image remotely/at a distance from the user/subject. For instance, the device 100 can be hung at a desktop monitor.

The method as described above is embodied as a computer implemented method in which a computer or programmable processor is used which executes a computer readable program. Further the computer readable program is embodied in a computer program product, such as random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, the RAM may include, for example, static random access memory (SRAM), dynamic random access memory (DRAM), or magnetic random access memory (MRAM) and other such devices. The ROM may include, for example, a programmable read-only memory (PROM), an erasable programmable read-only memory (EPROM), and an electrically erasable programmable read-only memory (EEPROM), another like memory device. The computer program product can also be an application (app) that can be installed on a computer/a wireless communication device/a portable electronic device/wearable device.

The memory unit 116 may include both volatile and/or nonvolatile memory and data storage components. Volatile components are those that do not retain data values upon loss of power. Nonvolatile components are those that retain data upon a loss of power. Thus, the memory may include, for example, random access memory (RAM), read-only memory (ROM), hard disk drives, solid-state drives, and/or other memory components, or a combination of any two or more of these memory components. In addition, the RAM may include, for example, static random access memory (SRAM), dynamic random access memory (DRAM), or magnetic random access memory (MRAM) and other such devices. The ROM may include, for example, a programmable read-only memory (PROM), an erasable programmable read-only memory (EPROM), and an electrically erasable programmable read-only memory (EEPROM), another like memory device. The memory unit 116 is a computer readable medium.

The term controller unit 108, as used herein, may be any type of controller or processor, and may be embodied as one or more controllers or processors adapted to perform the functionality discussed herein. Additionally, as the term processor is used herein, a processor may include use of a single integrated circuit (IC), or may include use of a plurality of integrated circuits or other components connected, arranged or grouped together, such as controllers, microprocessors, digital signal processors, parallel processors, multiple core processors, custom ICs, application specific integrated circuits, field programmable gate arrays, adaptive computing ICs, associated memory, such as and without limitation, RAM, DRAM and ROM, and other ICs and components.

Figure 5:
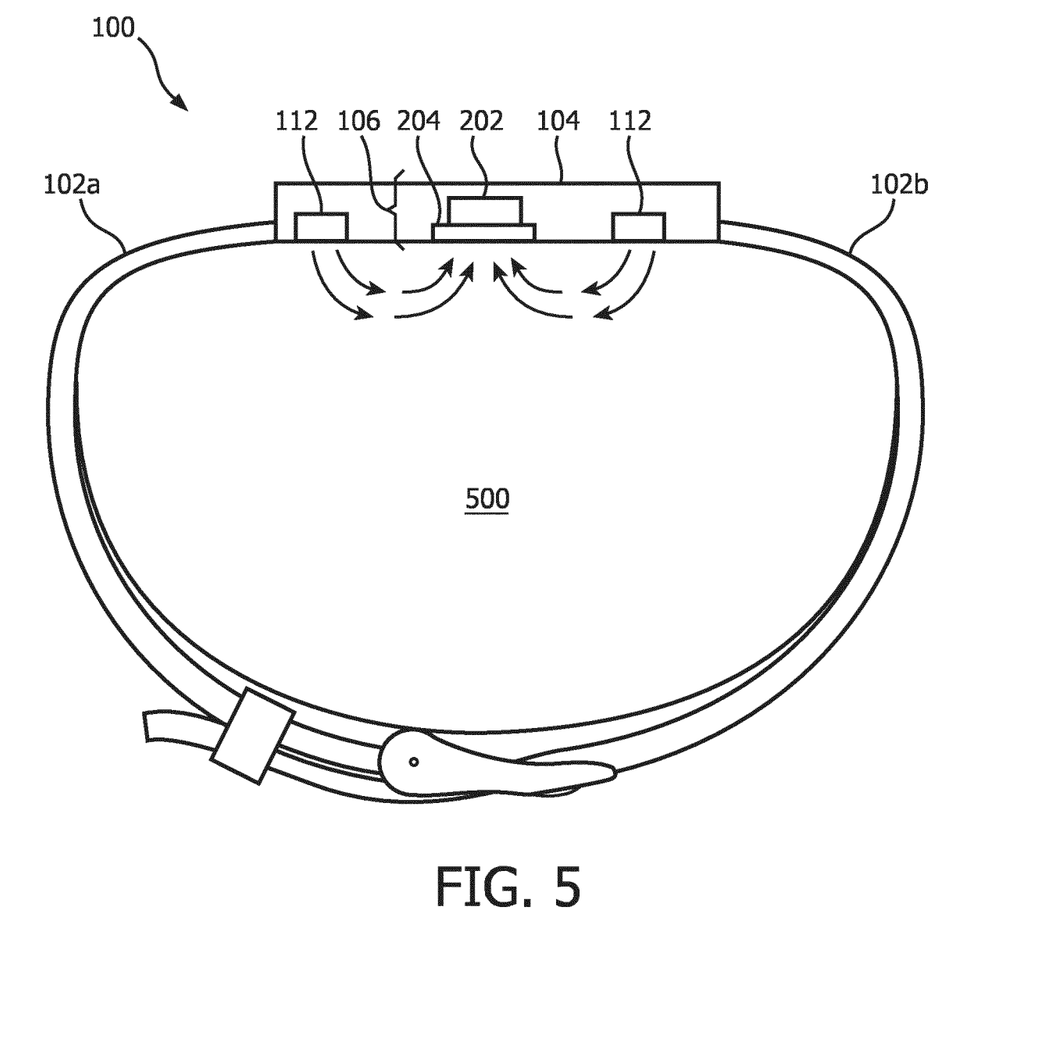
FIG. 5 shows a methodology employed by the controller unit to derive the PPG signal in the contact mode.
Figure 6:
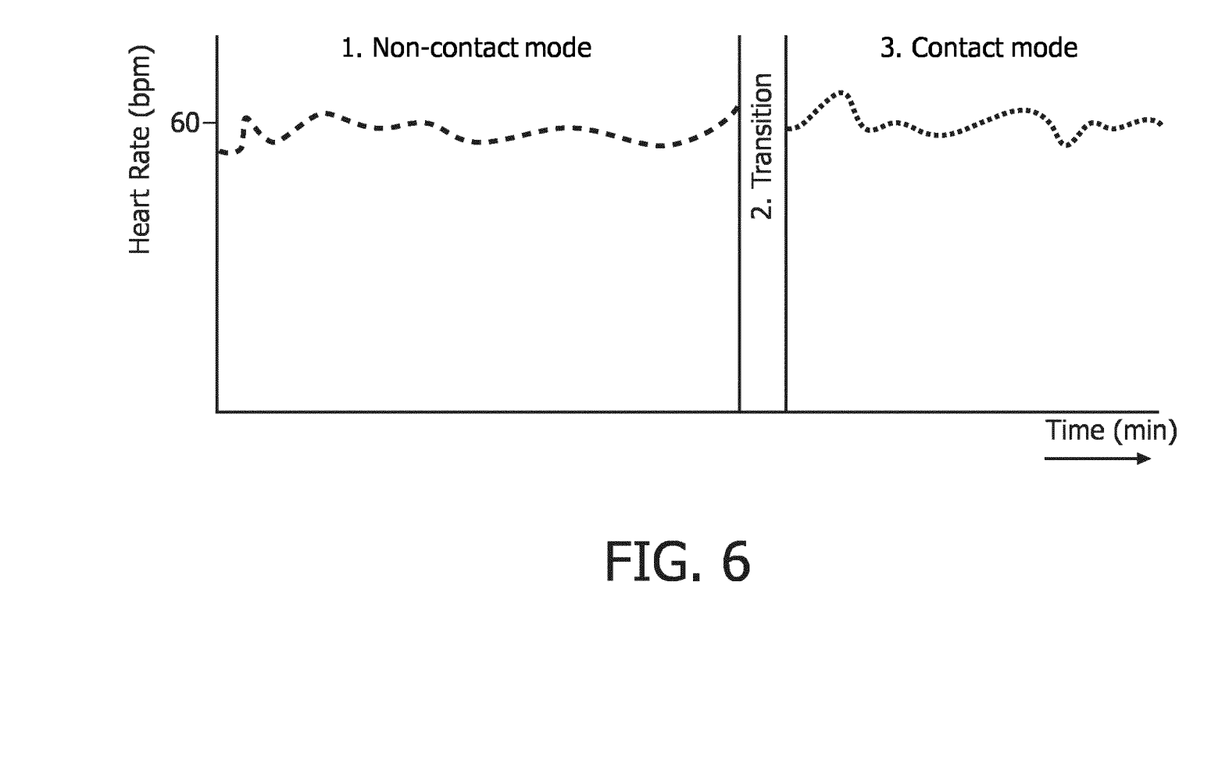
FIG. 6 shows an exemplary graph depicting continuous monitoring of heart rate.

FIG. 5 shows a methodology employed by the controller unit 108 to derive the PPG signal in the contact mode. As depicted in the figure the device 100 is in the contact mode. In the current embodiment of the invention, the device 100 is worn around the wrist 500 of the subject. The imaging unit 106 further includes a camera 202 and an image forming lens 204. In the current embodiment of the invention, the housing 104 can be connected with two parts (102a; 102b) of the band 102 by a click mechanism. In the current embodiment the camera 202, also may be referred to as camera array, is used as single element sensor. The illumination unit 112, such as a LED, illuminates the wrist 500 of the subject (depicted by arrows). Thereafter, the imaging unit 106 captures the sequence of images and subsequently the controller unit 108 (not depicted in the figure) will average all the all pixel values from the images to provide a PPG signal. The PPG signal thus provided is similar to the PPG signal detected by the single element sensor, such as a photo diode. Furthermore, calculation of HR from the PPG signal derived from photo diodes is already well known in the field of optical heart rate sensing. Similar process would apply once the PPG signal is obtained. In an alternate embodiment of the invention, the lens 204 can be absent and the camera can still acquire images, though blurred, from which the PPG signal can be derived.

FIG. 7a-e shows a device 700 for continuous monitoring of a subject according to an alternate embodiment of the invention. In the current embodiment (FIG. 7a), the device body 104 is removably connected with the band 102.

Figure 7A:
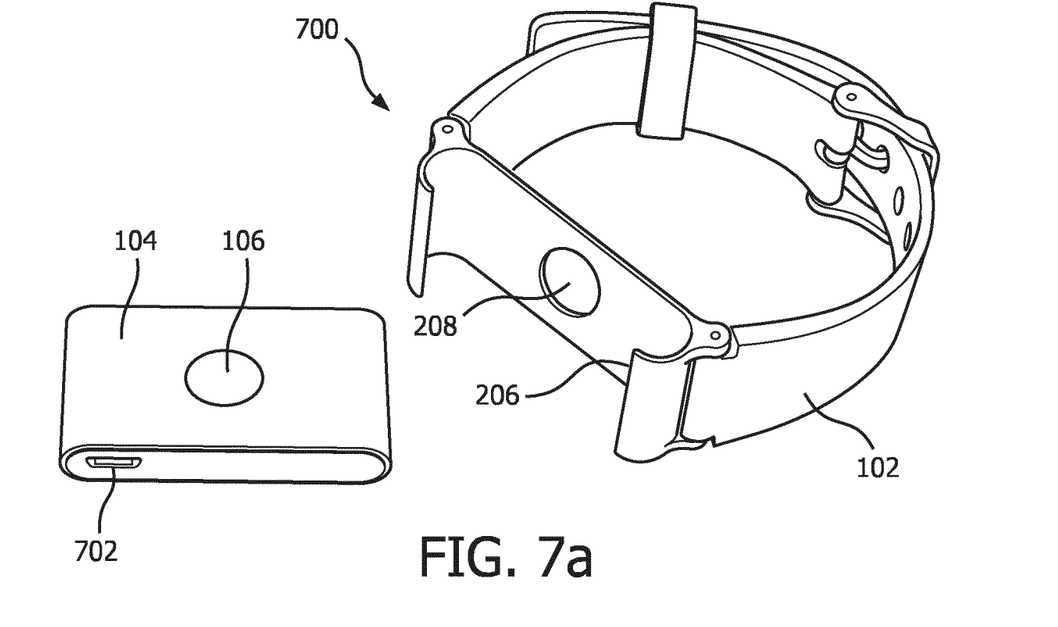
FIGS. 7a, 7b, 7c, 7d and 7e show a device for continuous monitoring of a subject according to an alternate embodiment of the invention.

The device body 104 includes the imaging unit 106, a controller unit 108 (not shown in the figures), an ambient light sensor 110 (not shown in the figures), an illumination unit 112 (not shown in the figures), an accelerometer 114 (not shown in the figures), a memory unit 116 (not shown in the figures), one or more batteries 118 (not shown in the figures) and a display unit 120 (not shown in the figures).

Figure 7B:
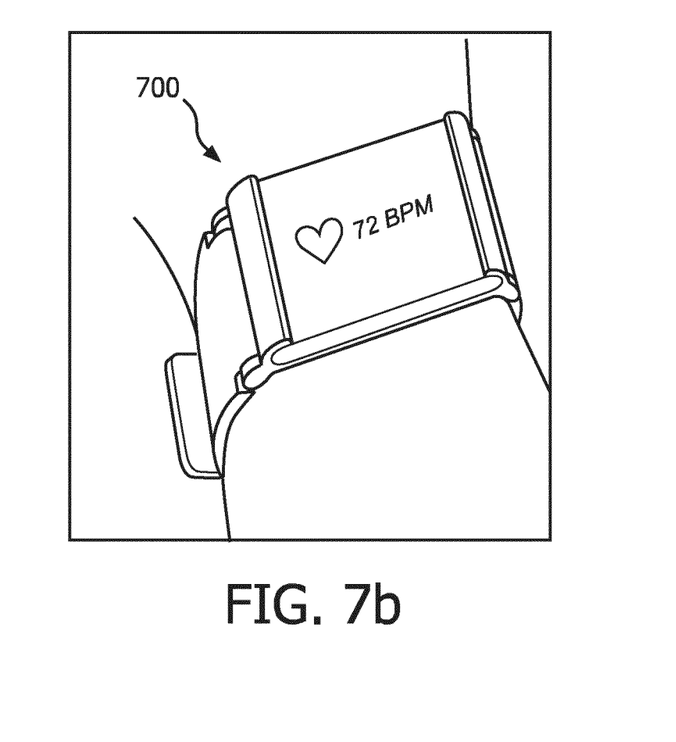
Figure 7C:
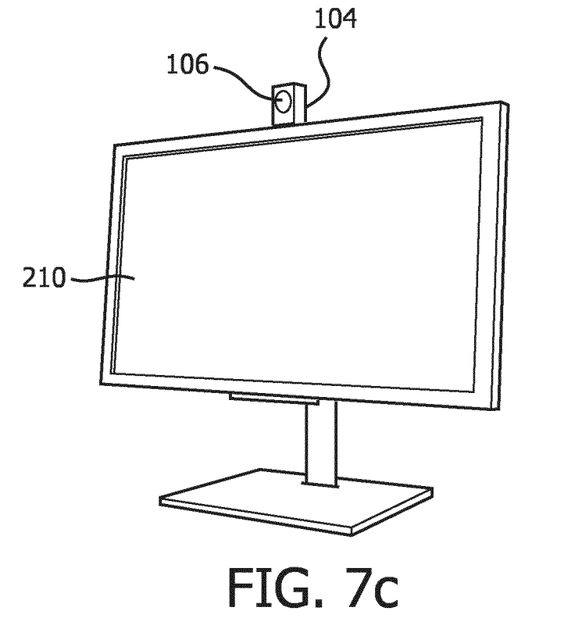
Figure 7D:
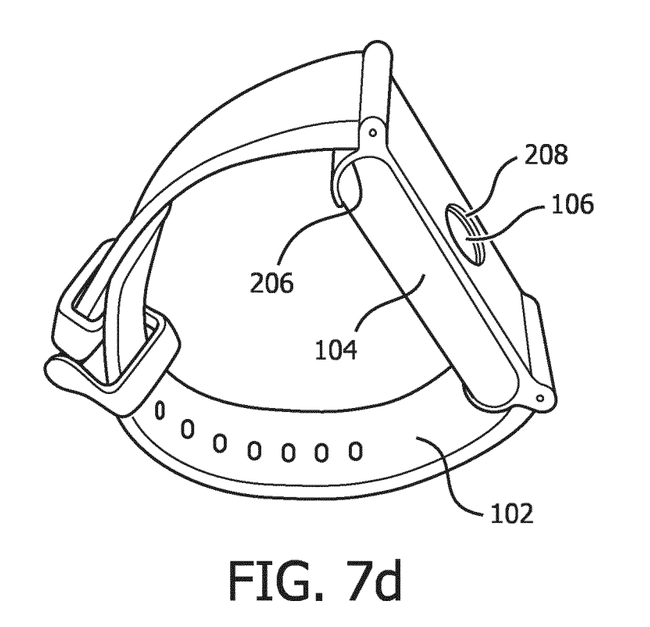
Figure 7E:
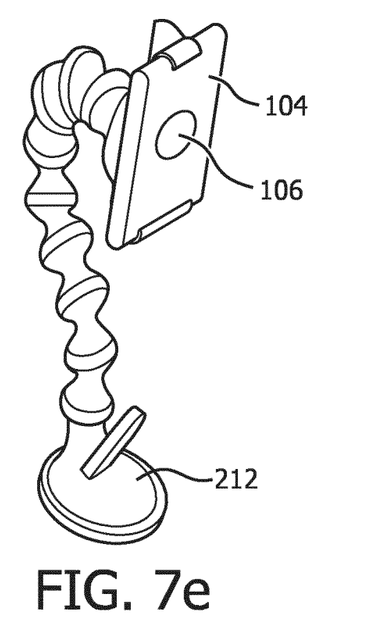

The band 102 includes a recess 206 to receive the housing 104. In the current embodiment of the invention, the housing 104 can be snap fitted/slid from the side into the recess 206. Other means of connection can be envisaged by a person skilled in the art. The band 102 further includes an aperture 208. The aperture 208 is included in the band 102 so that the imaging unit 106 can look/view the skin of the user for acquiring the images. Thus, in the contact mode as depicted in FIG. 7b, the imaging unit 106 will be facing downwards, through the aperture 208, to acquire the sequence of images from the wrist of the subject. Alternatively, the user can remove the housing 104 and place it in the recess 206 by turning it around, such that the imaging unit 106 can view towards the subject from a distance. Furthermore, as depicted in the FIG. 7c, the removable housing 104, can be placed on another entity 210, such a desktop monitor, such that imaging unit 106 faces the subject and thereby acquires the sequence of images for further processing by the controller unit 108. Various means such as magnetic connection, clips, etc. can be used to attach the housing 104 to the another entity 210. In an alternate embodiment of the invention, the band 102 can be designed such that the band 102 along with the housing 104 connected in the band 102 can be used in the non-contact mode (FIG. 7d). In this configuration the band 102 can be adjusted and placed such that the imaging unit 106 views from the aperture 208 to the outside in order to capture images from a distance. This avoids need of any other entity for attachment purposes. Another way to place the removable housing 104 is depicted in FIG. 7e, wherein the removable housing 104 is docked in a docking station 212 (another entity). In any of the embodiments mentioned above, in the non-contact mode while the imaging unit 106 captures the images from a distance, the one or more batteries 118 can be simultaneously charged, for instance through a USB connector 702.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an"

does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A wearable device for continuous health monitoring, the wearable device comprising:
    (a) a band for conforming to a first body part of a subject;
    (b) an imager, the imager being connected in the band, wherein the imager acquires a sequence of images from the subject's body, wherein the device is operable in a contact mode and in a non-contact mode,
        (i) wherein, in the contact mode, the wearable device is in contact with the skin of the first body part of the subject, and wherein the imager is in proximity to the first body part of the subject such that images of the area of the first body part can be captured by the imager, so as to acquire the sequence of images of an area of the first body part;
        (ii) wherein in the non-contact mode the imager is in a remote position to acquire the sequence of images of a second body part of the subject; and
    (c) a controller for deriving a photoplethysmography (PPG) signal from the acquired sequence of images according to a first process in the contact mode and according to a second process in the non-contact mode, the PPG signal being indicative of health of the subject;
    wherein the controller, during operation of the wearable device, checks at least one pre-determined condition in order to determine if the PPG signal is to be derived according to the first process or the second process and derives the PPG signal from the acquired sequence of images according to said determined process; wherein the at least one pre-determined condition is indicative of whether the device is to operate in the contact mode or the non-contact mode.

2. The wearable device according to claim 1, wherein the second body part is a face of the subject, wherein the controller detects presence of at least one facial feature of the subject in the acquired image in order derive the PPG signal according to the second process and wherein when presence of the at least one facial feature is not detected, the controller derives the PPG signal according to the first process, wherein detecting the presence or the non-presence of the at least one facial feature of the subject is the at least one pre-determined condition.

3. The wearable device according to claim 1, further comprising an ambient light sensor for sensing an ambient light, wherein the controller derives the PPG signal according to the second process when the ambient light is above a pre-determined ambient light threshold and wherein when the ambient light is below the pre-determined ambient light threshold, the controller derives the PPG signal according to the first process, wherein checking the ambient light is above or below the pre-determined ambient light threshold is the at least one pre-determined condition.

4. The wearable device according to claim 1, wherein the imager is removably connected to the band.

5. The wearable device according to claim 4, wherein the band comprises an aperture, the removable imager being placed, in the contact mode, above the aperture such that the imager is able to acquire the sequence of images from the area of the subject which is in front of the aperture.

6. The wearable device according to claim 4, wherein the removable imager acquires the sequence of images from being attached to another entity, the another entity being different than the band.

7. The wearable device according to claim 1, wherein the controller further derives a vital sign information from the PPG signal derived from acquired sequence of images in each mode.

8. The wearable device according to claim 1, wherein the imager in communication with the controller further recognizes the subject in the non-contact mode by detecting one or more facial features of the subject.

9. The wearable device according to claim 1, further comprising an illuminator for illuminating the subject's skin in the contact mode.

10. The wearable device according to claim 9, wherein the controller checks if a PPG signal is derivable from the sequence of images in the contact mode, wherein the controller switches off the illumination unit in absence of the PPG signal.

11. The wearable device according to claim 1, further comprising an accelerometer to provide motion information of the subject, wherein the controller instructs the imager to acquire the sequence of images in the contact mode upon receiving motion information.

12. The wearable device according to claim 1, wherein the wearable device is a wrist worn device arranged to acquire the sequence of images from a wrist of the subject, the wrist being the first body part.

13. The wearable device according to claim 1, wherein in the non-contact mode, the controller provides feedback to the subject such that the subject can place the imager in a preferred position, wherein the preferred position is a position in which the imager captures facial features of the subject in order to acquire the sequence of images.

14. A method for continuous health monitoring, the method comprising:
    (a) acquiring a sequence of images from the subject's body, wherein the images are being acquired by an imager, wherein the imager is either placed in a contact mode or in a non-contact mode,
        wherein in the contact mode, the wearable device is in contact with the skin of the first body part of the subject, and wherein the imager is in proximity to a first body part of the subject such that images of the area of the first body part can be captured by the imager, so as to acquire the sequence of images of an area of the first body part, and wherein a first process is used by a controller to derive a photoplethysmography (PPG) signal in the contact mode; and
        wherein, in the non-contact mode, the imager is in a remote position to acquire the sequence of images of a second body part of the subject, and wherein a second process is used by the controller to derive a PPG signal in the non-contact mode;
    (b) checking at least one pre-determined condition that is indicative of whether the imager is placed in the contact mode or the non-contact mode, the check being performed by the controller; and (c) deriving the PPG signal according to the first process or the second process based on the outcome of the check, wherein the PPG signal is derived by the controller.

15. A non-transitory computer-readable medium that stores therein a computer program product, which, when executed on a processor, causes the processor to:
(a) acquire a sequence of imager from the subject's body, wherein the images are being acquired by an imager, wherein the imager is either placed in a contact mode or in a non-contact mode,
  wherein, in the contact mode, the wearable device is in contact with the skin of the first body part of the subject, and wherein the imager is in proximity to a first body part of the subject such that images of the area of the first body part can be captured by the imager, so as to acquire the sequence of images of an area of the first body part, and wherein a first process is used by a controller to derive a photoplethysmography (PPG) signal in the contact mode, and
  wherein, in the non-contact mode, the imager is in a remote position to acquire the sequences of images of a second body part of the subject, and wherein a second process is used by the controller to derive a PPG signal to the non-contact mode;
(b) check at least one pre-determined condition that is indicative of whether the imager is placed in the contact mode or the non-contact mode, the check being performed by the controller; and
(c) derive the PPG signal according to the first process or the second process based on the outcome of the check, wherein the PPG signal is derived by the controller.

* * * * *